United States Patent [19]

Costanzi et al.

[11] Patent Number: 4,898,946
[45] Date of Patent: Feb. 6, 1990

[54] PROCESS FOR THE PREPARATION OF N-ALLYL-PIPERIDINE DERIVATIVES

[75] Inventors: Silvestro Costanzi, San Giuliano Milanese; Damiano Gussoni, Milan; Luciano Pallini, Fornovo di Taro, all of Italy

[73] Assignee: Enichem Synthesis S.p.A., Palermo, Italy

[21] Appl. No.: 56,880

[22] Filed: Jun. 3, 1987

[30] Foreign Application Priority Data

Jun. 11, 1986 [IT] Italy .................. 20756 A/86

[51] Int. Cl.⁴ .......................................... C07D 211/40
[52] U.S. Cl. .................... 546/216; 546/217; 558/277
[58] Field of Search ............... 546/217, 216; 558/277

[56] References Cited

U.S. PATENT DOCUMENTS 4,014,887  3/1977  Randell et al. ............ 546/216
4,307,032 12/1981  Krimm et al. ............ 558/277
4,426,331  1/1984  Drent ......................... 558/277

OTHER PUBLICATIONS

Bäckvall et al., "Tetrahedron Letters", vol. 24, No. 4 pp. 411-412 (1983).
Guibe et al., "Tetrahedron Letters", vol. 22, No. 37, pp. 3591-3594 (1981).
Tsuji, J., "Organic Synthesis with Palladium Compound", Springer Verlag, Berlin (1980), p. 125.

*Primary Examiner*—Glennon H. Hollrah
*Assistant Examiner*—B. K. Trinh
*Attorney, Agent, or Firm*—Stevens, Davis, Miller & Mosher

[57] ABSTRACT

A process is described for the preparation of N-allyl-2,2,6,6-tetraalkyl-piperidine derivatives which involves reaction of the corresponding 2,2,6,6-tetraalkyl-piperidine with an allylic carbonate in the presence of palladium catalysts. The products which are thus obtained are useful as polymer stabilizers and chemical intermediates.

11 Claims, No Drawings

PROCESS FOR THE PREPARATION OF N-ALLYL-PIPERIDINE DERIVATIVES

The present invention refers to a process for the synthesis of N-allyl-2,2,6,6-tetraalkyl-piperidine derivatives of general formula I

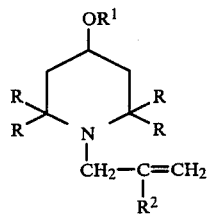

wherein R is $(C_1-C_4)$alkyl, $R^1$ is hydrogen, straight or branched $(C_1-C_{20})$alkyl, straight or branched $(C_3-C_{20})$alkenyl or phenyl-$(C_1-C_6)$alkyl and $R^2$ is hydrogen or methyl.

Variously 4-substituted 2,2,6,6-tetramethyl-piperidine derivatives bearing an allyl group on the piperidine nitrogen atom are described and claimed in German Offenlegungsschrift 2,258,752.

In said patent application, preparation of 4-allyloxy-1-allyl-2,2,6,6-tetramethyl-piperidine is accomplished through allylation of 4-allyloxy-2,2,6,6-tetramethyl-piperidine with allyl bromide, wherein the starting 4-allyloxy-2,2,6,6-tetramethyl-piperidine also acts as acceptor of the hydrobromic acid which forms during the reaction, thus drastically reducing the reaction yield. Besides said conventional method, also reported in literature is the synthesis of N-allyl derivatives through reaction of allyl alcohols, esters or ethers with primary or secondary amines in the presence of palladium catalysts (J. Tsuji - "Organic Synthesis with Palladium Compounds", Springer Verlag, Berlin (1980), p. 125). However, when these reactants, and particularly allyl alcohol, di-allyl ether and allyl acetate are employed in the presence of palladium catalysts in the N-allylation of a 4-substituted-2,2,6,6-tetraalkyl-piperidine, the results which are obtained are highly disappointing. The desired 4-substituted N-allyl-2,2,6,6-tetraalkyl-piperidine derivative is in fact obtained in less than 5% yield.

It has now surprisingly been found, and represents the object of the present invention, that optimum results are obtained in the palladium-catalyzed N-allylation of 4-substituted-2,2,6,6-tetraalkyl-piperidine derivatives, when an allylic carbonate is employed as the allylating agent.

These results are surprising not only because, as anticipated, the allylation reaction carried out under the same conditions but using the conventional allylating agents does not afford satisfacory results but also because it is known (see Tetrahedron Lett. 22 (1981), pp. 3591-4 and Tetrahedron Lett. 24 (1983), pp. 411-2) that allylic carbonates easily decarboxylate in the presence of palladium catalysts, even in very mild conditions, yielding the corresponding ether. Contrary to what could be expected on the basis of the prior art, the process of the present invention, which consists in the reaction of a 2,2,6,6-tetraalkyl-piperidine derivative with an allylic carbonate in the presence of a palladium catalyst, makes it possible to get the desired N-allyl derivatives of formula I in very high yields and almost complete selectivity. More particularly, the N-allylation process according to the present invention, smoothly proceeds by contacting the 4-substituted 2,2,6,6-tetraalkyl-piperidine substrate with an at least equimolar amount of a carbonate of formula III

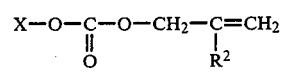

wherein X is a $-CH_2-C(R^2)=CH_2$, $(C_1-C_4)$alkyl or aryl-$(C_1-C_4)$alkyl group, and $R^2$ is as defined above, in the presence of a palladium catalyst.

Palladium catalysts which may conveniently be used in the above reaction are, for instance, finely divided metallic palladium, supported on an inert material such as for instance carbon or asbestos, palladium chloride $[Pd(Cl)_2[$, palladium diacetate $[Pd(OAc)_2]$, palladium diacetylacetonate $[Pd(acac)_2]$ and trialkyl- or triarylphosphine complexes of zerovalent palladium or of palladium compounds [e.g. $Pd(PPh_3)_3$, $Pd(PPh_3)_4$, $PdCl_2(PPh_3)_2$, $Pd(acac)_2(PPh_3)_2]$.

The amount of palladium catalyst which may suitably be employed depends onthe nature of the catalyst itself. As an example, when 5% Pd/C is used, this will typically be employed in percentages by weight (calculated on the weight of the starting piperidine substrate) ranging from 2 to 25, while, when, for instance, $Pd(Cl)_2$, $Pd(acac)_2$, $Pd(Cl)_2(PPh_3)_2$ or $Pd(PPh_3)_4$ are employed, these may suitably be used in percentages by weight down to 0.5.

In particular, when a palladium complex is used containing triphenylphosphine as the ligand, is it advisable to work with catalyst percentages lower than 5, and, more preferably, lower than 1, in order to avoid decarboxylation of the allylic carbonate which is particularly relevant in the presence of the $Pd(PPh_3)_4$ complex. In these cases, furthermore, it is advisable to carry out the addition of the allylic carbonate to the reaction mixtue containing the piperidine substrate and the phosphine-containing catalyst, very slowly.

The reaction can be carried out in the presence of an inert organic solvent eithe apolar or, preferably, polar aprotic, such as for instance, toluene, xylene, tetrahydrofuran, dimethylsulfoxide, dimethylformamide, acetonitrile, benzonitrile and the like solvents, or it may be carried out in the absence of any organic solvent, using, in this case, an excess allylic carbonate to dissolve the piperidine substrate. The reaction is carried out in an inert atmosphere, typically under nitrogen atmosphere, suitably degassing the solvent, if any.

The temperature of the reaction is generally between room temperature and 140° C and, preferably, between 40 and 120° C.

At the end of the reaction, which is generally complete in a few hours, and whose course can be monitored by gas-chromatography, the desired N-allyl piperidine derivative is recovered through conventional methods which depend both on the particular product and on the catalyst employed and which will involve possible separation of the catalyst, removal of the solvent, if any, and of the starting compounds or low-boiling by-products followed by purification of the product by fractional distillatin or crystallization.

The following examples which illustrate in detail the process of the present invention, are not to be construed as a limitation to the scopes thereof.

EXAMPLE 1

2,2,6,6-tetramethyl-piperidin-4ol (1 g, 6.37 mmol), di-allyl carbonate (3 g, 21 mmol) and 5% Pd/C (0.2 g) are charged into a 10 ml-flask kept under nitrogen atmosphere.

The reaction mixture is then heated to 110° C. and stirred at this temperature for 8 hours. Gas-chromatographic analysis of the filtered solution shows that the desired product, i.e. 1-allyl-2,2,6,6-tetramethyl-piperidinol, is obtained in 75% yield (calculated on the starting piperidinol) and 97-98% selectivity.

EXAMPLE 2

2,2,6,6-tetramethyl-piperidin-4ol (0.5 g, 3.18 mmol), $PdCl_2$ (20 mg, 0.11 mmol) and di-allyl carbonate (5 ml, 36 mmol) are charged, under inert atmosphere, into a 10 ml-flask equipped with a reflux condenser. The reaction mixture is then heated to 110° C. under stirring for about 6 hours. Gas-chromatographic analysis shows that the reaction afforded the desired 1-allyl-2,2,6,6-tetramethyl-piperidin-4ol in 85% yield (calculated on the starting piperidinol) and >98% selectivity.

EXAMPLE 3

4-allyloxy-2,2,6,6-tetramethyl-piperidine (150 g, 0.76 mol), $Pd(Ac)_2$ (0.25 g, 1.12 mmol) triphenylphosphine (1.17 g, 4.46 mmol) and toluene (100 ml) are charged, under nitrogen atmosphere, into a 3-necked 500 ml-flask equipped with a dropping funnel, a thermomete, and a reflux condenser. Di-allyl carbonate (150 g, 1.05 mol) is then added dropwise, over 4 hours, to the thus obtained mixture stirred at 50°;0 C. When the evolution of carbon dioxide subsides (about 5 hours from the beginning) gas-chromatographic analysis of the reaction mixture shows that the desired compound, i.e. 1-allyl-4-allyloxy-2,2,6,6-tetramethyl-piperidine, is obtained in 77% yield (calculated on the starting 4-allyloxy-2,2,6,6-tetramethyl-piperidine) and >98% selectivity.

EXAMPLE 4

4-allyloxy-2,2,6,6-tetramethyl-piperidine (150 g, 0.76 mol), di-allyl carbonate (115 g, 0.8 mol) and $PdCl_2$ (1.35 g, 1.6 mmol) are charged under nitrogen atmosphere into a 3-necked 500 ml-flask equipped with a thermometer and a reflux condenser. The solution is heated under stirring to 110° C. for 24 hours. Gas-chromatographic analysis of the reaction mixture then shows that the reaction produced the desired 1-allyl-4-allyloxy-2,2,6,6-tetramethyl-piperidine in 63% yield (calculated on the starting 4-allyloxy-2,2,6,6-tetramethyl-piperidine) and >97% selectivity.

EXAMPLE 5

2,2,6,6-tetramethyl-piperidin-4-ol (12.5 g, 79.6 mmol), $Pd(Ac)_2$ (145 mg, 0.64 mmol), triphenylphosphine (0.6 g, 2.29 mmol) and tetrahydrofuran (40 ml) are charged under inert atmosphere in a 100 ml-flask equipped with a dropping funnel. The reaction mixture is heated under stirring to 50° C.

Di-allyl carbonate (20 g, 140 mmol) is then slowly added thereto over a period of two hours. After an additional hour, gas-chromatographic analysis of the reaction mixture shows that the obtained mixture has the following composition:
2,2,6,6-tetramethyl-piperidin-4-ol: 3%,
4-allyloxy-2,2,6,6-tetramethylpiperidine: 3%,
1-allyl-4-allyloxy-2,2,6,6-tetramethyl-piperidine: 7.5%,
1-allyl-2,2,6,6-tetramethyl-piperidin-4-ol: 86%.

EXAMPLE 6 (PRIOR-ART METHOD)

2,2,6,6-tetramethyl-piperidin-4-ol (25 g, 0.16 mol), 1,2-dimethoxyethane (130 ml), and allyl bromide (35 ml, 0.4 mol) are charged into a glass, pressure-resistant, reaction vessel equipped with a manometer.

The solution, vigorously stirred, is heated to 120° C. for 5 hours. Piperidin-4-ol hydrobromide separates during the reaction. The reaction mixture is then cooled to room temperature and water (150 ml) and ethyl ether (100 ml) are added thereto. The organic phase is separated, washed carefully with water and dried over $MgSO_4$. Upon evaporating off the organic solvent and excess allyl bromide, a residue is obtained (14.5 g) consisting of 1-allyl-2,2,6,6-tetramethyl-piperidin-4-ol corresponding to 47% yield (calculated on the starting piperidin-4-ol) and 50% selectivity.

We claim:

1. A process for preparing a 2,2,6,6-tetraalkyl-piperidine derivative of general formula I

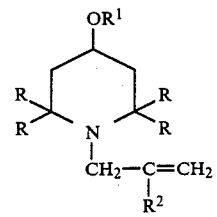

wherein R is $(C_1-C_4)$alkyl, $R^1$ is hydrogen, straight or branched $(C_1-C_{20})$alkyl, straight or branched $(C_3-C_{20})$alkenyl or phenyl-$(C_1-C_6)$alkyl and $R^2$ is hydrogen or methyl, which comprises reacting a 2,2,6,6-tetraalkyl-piperidine derivative of formula II

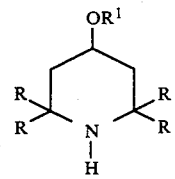

wherein R and $R^1$ are as defined above with an allylic carbonate of formula III

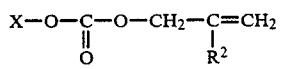

wherein X is a $-CH_2-C(R^2)=CH_2$, $(C_1-C_4)$alkyl or aryl-$(C_1-C_4)$alkyl group, and $R^2$ is as defined above, in the presence of a palladium catalyst.

2. The process of claim 1 wherein the catalyst is selected from the group consisting of supported metallic palladiu, $PdCl_2$, $Pd(OAc)_2$, $Pd(acac)_2$, and the trialkyl- or triaryl-phosphine complexes of zerovalent palladium or of palladium compounds.

3. The process of claim 2 wherein the catalyst is employed in percentages by weight comprised between 0.5 and 25 with respect to the weight of the starting piperidine substrate.

4. The process of claim 1 wherein at least an equimolar amount of the allylic carbonate of formula III is employed.

5. The process of claim 4 wherein an excess of the allylic carbonate of formula III is employed.

6. The process of claim 5 wherein the reaction is carried out in the absence of any organic solvent.

7. The process of claim 1 wherein the reaction is carried out in the presence of an inert organic solvent selected from the classes of apolar and polar aprotic solvents.

8. The process of claim 7 wherein the solvent is selected from the group consisting of toluene, xylene, tetrahydrofuran, dimethylsulfoxide, dimethylformamide, acetonitrile, and benzonitrile.

9. The process of clam 1 wherein the reaction is carried out at a temperature between room temperature and 140° C.

10. The process of claim 9 wherein the temperature is between 40 and 120° C.

11. The process of any of the preceding claims for preparing a compound of formula I wherein R is methyl.

* * * * *